United States Patent
Esaki et al.

(10) Patent No.: US 7,135,306 B2
(45) Date of Patent: Nov. 14, 2006

(54) METHOD OF MEASURING HOMOCYSTEINE

(75) Inventors: Nobuyoshi Esaki, Shiga (JP); Tohru Yoshimura, Kyoto (JP); Naoto Matsuyama, Osaka (JP); Koji Mizuno, Osaka (JP); Takayuki Bogaki, Hyogo (JP); Toshitaka Minetoki, Hyogo (JP); Kenji Ozeki, Hyogo (JP)

(73) Assignee: Alfresa Pharma Corproation, Osaka (JP)

( * ) Notice: Subject to any disclaimer, the term of this patent is extended or adjusted under 35 U.S.C. 154(b) by 0 days.

(21) Appl. No.: 10/546,089

(22) PCT Filed: Jan. 28, 2004

(86) PCT No.: PCT/JP2004/000787
§ 371 (c)(1),
(2), (4) Date: Aug. 19, 2005

(87) PCT Pub. No.: WO2004/074477
PCT Pub. Date: Sep. 2, 2004

(65) Prior Publication Data
US 2006/0166300 A1    Jul. 27, 2006

(30) Foreign Application Priority Data
Feb. 19, 2003 (JP) .............................. 2003-041585

(51) Int. Cl.
*C12Q 1/34* (2006.01)
*C12Q 1/37* (2006.01)
*G01N 33/53* (2006.01)

(52) U.S. Cl. .............................. 435/18; 435/23; 435/24; 435/25

(58) Field of Classification Search .................. 435/18, 435/23, 24, 25
See application file for complete search history.

(56) References Cited

U.S. PATENT DOCUMENTS

| | | | |
|---|---|---|---|
| 5,478,729 A | 12/1995 | Van Atta et al. | |
| 6,306,618 B1 | 10/2001 | Coombs et al. | |
| 6,686,172 B1* | 2/2004 | Matsuyama et al. | 435/18 |
| 6,867,012 B1 | 3/2005 | Kishimoto et al. | |

OTHER PUBLICATIONS

Fukushima, Takeshi et al., "Determination of D-Amino Acids in Serum from Patients with Renal Dysfunction", Biol. Pharm. Bull., 1995, pp. 1130-1132, vol. 18, No. 8.

Bergey's Manual of Determinative Bacteriology, 8th Ed., edited by R.E. Buchanan and N.E. Gibbons, 1974, pp. 295-296, publisher The Williams & Wilkins Company, Baltimore, MD.

Zawadzke, Laura E. et al., "Existence of Two D-Alanine:D-Alanine Ligases in *Escherichia coli*: Cloning and Sequencing of the ddlA Gene and Purification and Characterization of the DdlA and DdlB Enzymes", Biochemistry, 1991, 30, pp. 1673-1682, Amer. Chemical Society.

Robinson, Arthur C. et al., "Further Evidence for Overlapping Transcriptional Units in an *Escherichia coli* Cell Envelope-Cell Division Gene Cluster: DNA Sequence and Transcriptional Organization of the ddl ftsQ Region", Journal of Bacteriology, vol. 167, No. 3, Sep. 1986, pp. 809-817, publ. American Society for Microbiology.

McFall, Elizabeth et al., "DNA Sequences of the D-Serine Deaminase Control Region and N-Terminal Portion of the Structural Gene", Journal of Bacteriology, Jun. 1983, pp. 1508-1512, vol. 154, No. 3, publ. American Society for Microbiology.

Hanahan, Douglas, "Studies on Transformation of *Escherichia coli* with Plasmids", J. Mol. Biol. 1983, vol. 166, pp. 557-580, publ. Academic Press Inc. (London).

Grue-Sorensen, Gunnar et al., "Diastereospecific, Enzymically Catalysed Transmethylation from *S*-Methyl-L-methionine to L-Homocysteine, a Naturally Occuring Process", J. Chem. Soc. Perkin Trans. vol. I, 1984, pp. 1091-1097.

Partial Translation of Seikagakujiten (Biochemistry Dictionary), 3d Ed., Tokyo Kagaku Dojin, 1998, p. 182, Editor: Kazutomo Imahori and Tamio Yamakawa (4 pp.).

Marceau, Michelle et al., "D-Serine Dehydratase from *Escherichia coli*, DNA Sequence and Identification of Catalytically Inactive Glycine to Aspartic Acid Variants", The Journal of Biological Chemistry, vol. 263, No. 32, Nov. 15, 1988, pp. 16926-16933, publ. The American Society for Biochemistry and Molecular Biology, Inc.

* cited by examiner

*Primary Examiner*—Susan Hoffman
*Assistant Examiner*—Paul Martin
(74) *Attorney, Agent, or Firm*—The Webb Law Frim

(57) ABSTRACT

A method for detecting or measuring homocysteine in a sample includes the steps of (a) reacting a D-amino acid present in a sample with a D-amino acid converting enzyme to convert the D-amino acid into a substance that does not serve as a substrate of D-amino acid oxidase or D-amino acid acetyltransferase; (b) reducing homocysteine in the sample with a thiol compound; (c) reacting the reduced homocysteine with a methyltransferase and a methyl donor to newly produce D-amino acid; and (d) reacting the produced D-amino acid with the D-amino acid oxidase or the D-amino acid acetyltransferase in the presence of an SH reagent to produce hydrogen peroxide, and color-developing the produced hydrogen peroxide by using an oxidative color-developing agent.

6 Claims, 5 Drawing Sheets

Fig. 6 (a) Prior Art
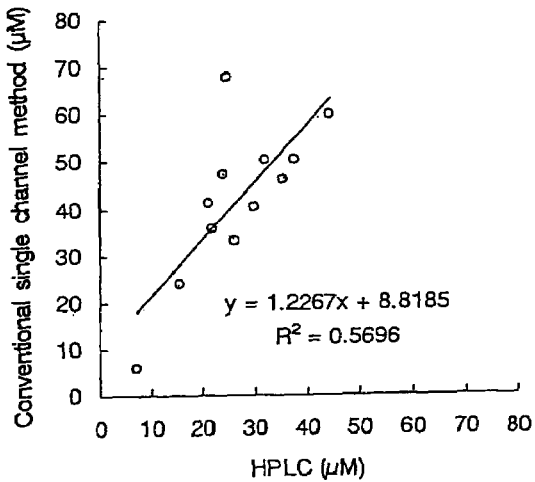
Fig. 6(b) Prior Art
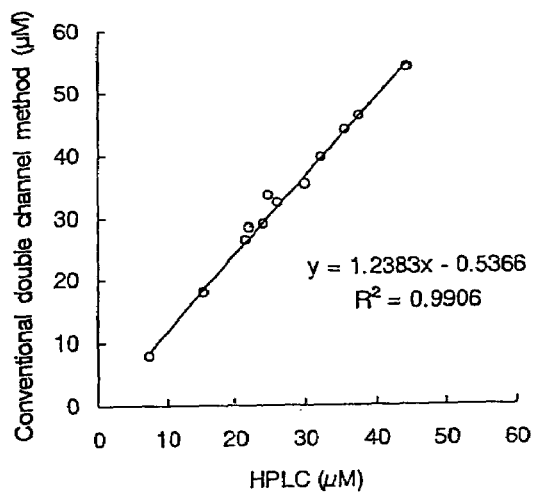
Fig. 6 (c)
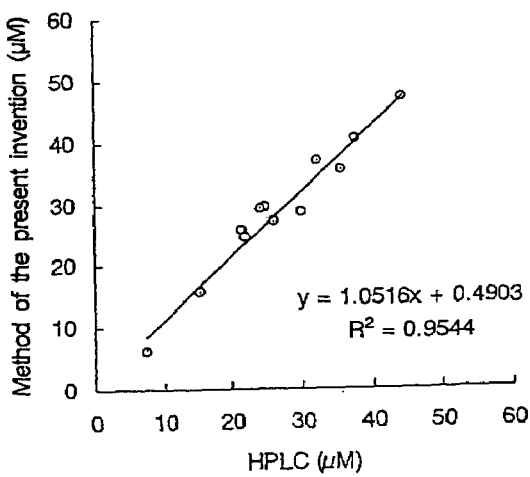

SEQUENCE LISTING

<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: primer

<400> SEQUENCE: 1
gcgaattcat ggaaaaactg cgggta                                    26

<210> SEQ ID NO 2
<211> LENGTH: 26
<212> TYPE: DNA
<213> ORGANISM: Artificial Sequence
<220> FEATURE:
<223> OTHER INFORMATION: primer

<400> SEQUENCE: 2
ggctgcagtt acattgtggt tttcaa                                    26

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
atgactgata aaatcgcggt c                                         21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ttagtccgcc agttccagaa t                                         21

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
ggtgaattca aagagacgta ctatggaaaa c                              31

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
ggtaagcttt tgcgatgctg cgttgaaacg                                30

METHOD OF MEASURING HOMOCYSTEINE

TECHNICAL FIELD

The present invention relates to a method of detecting or measuring homocysteine in a sample. More specifically, the present invention relates to a method of measuring homocysteine including the step of removing a D-amino acid present in a sample in advance.

BACKGROUND ART

As a method of measuring homocysteine, a method of reacting homocysteine in a sample with homocysteine methyltransferase and D-methionine methylsulfonium, and then detecting the produced D-methionine with D-amino acid oxidase has been reported (see WO 02/02802). However, it is known that biological samples contain D-amino acids such as D-alanine and D-serine in small amounts, and these amino acids increase in the case of renal diseases or the like (e.g., see Fukushima, T., Biol. Pharm. Bull., 1995, Vol. 18, No. 8, pp. 1130–1132). It is believed that D-alanine and D-serine, which can be a substrate of D-amino acid oxidase, leads to a positive reading in the method of measuring homocysteine. Therefore, as described in WO 02/02802, in order to avoid the influence of endogenous D-amino acids that are originally present in a sample, it is necessary to subtract a value obtained by measurement by the same operation except that homocysteine methyltransferase is not contained from a measured value in the case of containing this enzyme. That is to say, it is necessary to provide a sample blank for each individual sample to measure the amount of endogenous D-amino acids.

SUMMARY OF THE INVENTION

It is an object of the present invention to provide a method of measuring homocysteine that is not affected by endogenous D-amino acids, that is, that does not require sample blanks.

As a result of in-depth research in order to achieve the above object, it became possible to provide a method of measuring homocysteine that is not affected by endogenous D-amino acids, that is, that does not require sample blanks by leading D-alanine and/or D-serine to the outside of the reaction system of the homocysteine measurement by enzyme actions.

The present invention provides a method for detecting or measuring homocysteine in a sample, and the method includes the steps of: (a) reacting a D-amino acid present in a sample with a D-amino acid converting enzyme to convert the D-amino acid into a substance that does not serve as a substrate of D-amino acid oxidase or D-amino acid acetyltransferase; (b) reducing homocysteine in the sample with a thiol compound; (c) reacting the reduced homocysteine with a methyltransferase and a methyl donor to newly produce D-amino acid; and (d) reacting the produced D-amino acid with the D-amino acid oxidase or the D-amino acid acetyltransferase in the presence of an SH reagent to produce hydrogen peroxide, and color-developing the produced hydrogen peroxide by using an oxidative color-developing agent.

In a preferred embodiment, the step (a) is a step of reacting D-alanine present in a sample with D-alanyl-D-alanine ligase (which may be referred to "Ddl" hereinafter) in a presence of adenosine triphosphate to convert the D-alanine into D-alanyl-D-alanine and/or a step of reacting D-serine present in a sample with D-serine dehydratase (which may be referred to "Dsd" hereinafter) to convert the D-serine into pyruvic acid.

In a preferred embodiment, the methyltransferase is homocysteine methyltransferase, and the methyl donor is D-methionine methylsulfonium.

In a preferred embodiment, in the step (d), the produced hydrogen peroxide is detected or measured by color-development using peroxidase and an oxidative color-developing agent.

The present invention also provides a reagent kit for measuring homocysteine comprising D-alanyl-D-alanine ligase and/or D-serine dehydratase; a thiol compound; methyltransferase; a methyl donor; D-amino acid oxidase or D-amino acid acetyltransferase; an SH reagent; and an oxidative color-developing agent.

The present invention further provides a method for detecting or measuring homocysteine in a sample, comprising the steps of reacting a D-amino acid present in a sample with a D-amino acid converting enzyme to convert the D-amino acid into a substance that does not serve as a substrate of D-amino acid oxidase or D-amino acid acetyltransferase.

BRIEF DESCRIPTION OF DRAWINGS

FIGS. 6(a)–6(c) are graphs showing a correlation between the concentration of the measured homocysteine according to (a) a conventional single channel method, (b) a conventional double channel method, and (c) the method of the present invention and the concentration measured by a HPLC method.

DETAILED DESCRIPTION OF THE INVENTION

Figure 1:
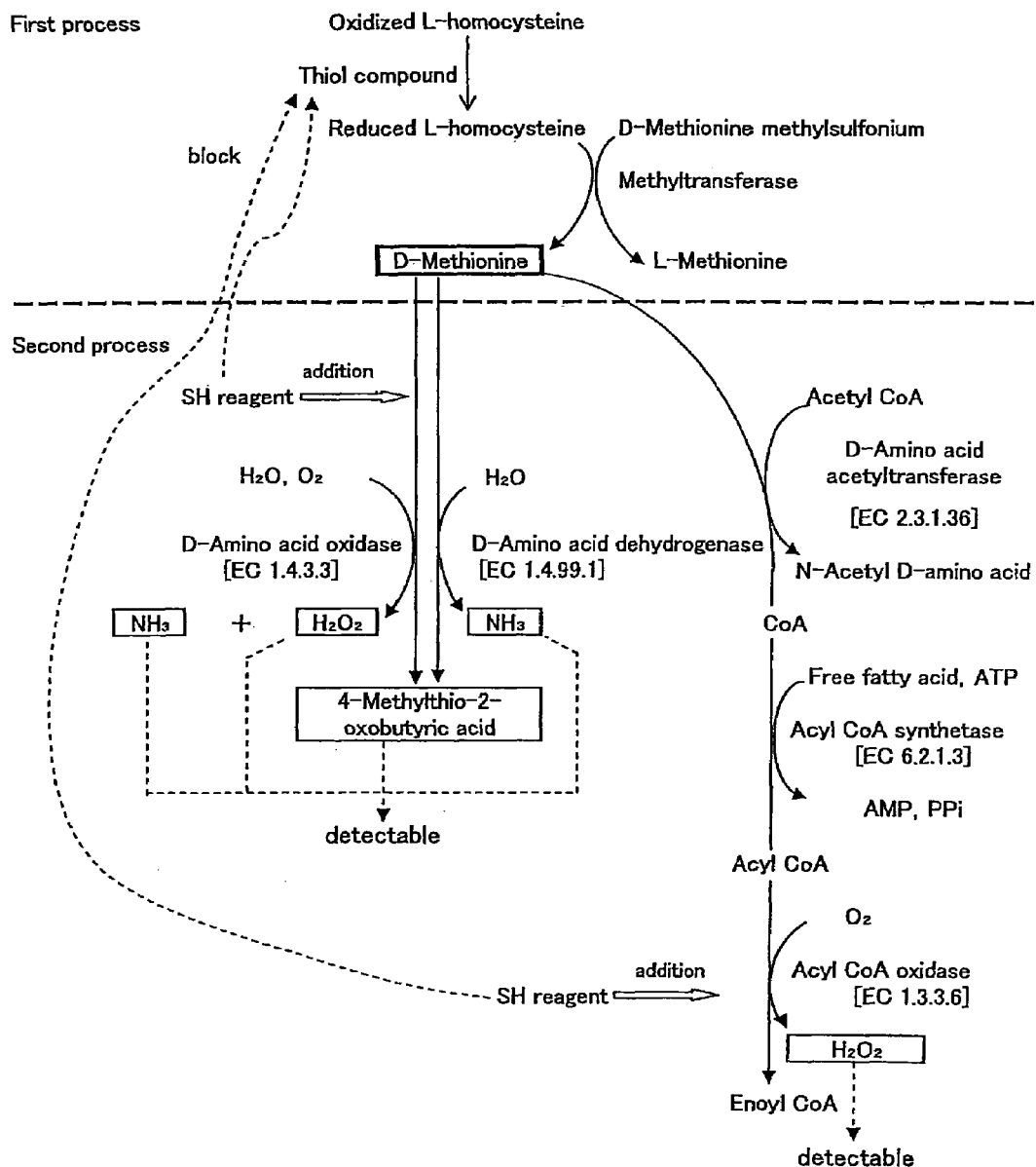
FIG. 1 is a schematic diagram of the reaction in a method of measuring homocysteine using homocysteine transferase and D-methionine methylsulfonium.

Principle of Homocysteine Measurement:

The method of measuring homocysteine of the present invention is based on the principle that homocysteine in a sample is subjected to a reduction treatment with a thiol compound, and is reacted with a methyltransferase in the presence of a methyl donor (first process), and then the produced D-amino acid or D-amino acid derivative is measured (second process). For example, as shown in FIG. 1, when D-methionine produced in the first process is reacted with D-amino acid oxidase in the second process, hydrogen peroxide is produced, and the hydrogen peroxide can be led to an oxidative color-developing agent commonly used in the presence of an SH reagent so as to be determined colorimetrically. When the D-methionine is reacted with D-amino acid acetyltransferase, the produced coenzyme A is led to hydrogen peroxide using acyl coenzyme A synthetase

[EC 6.2.1.3] and acyl coenzyme A oxidase [EC 1.3.3.6], and this can be determined in the same manner.

The method of detecting or measuring homocysteine of the present invention is characterized in that in order to eliminate the influence of endogenous D-amino acids when measuring D-amino acids, first, a D-amino acid present in a sample is reacted with a D-amino acid converting enzyme to convert the D-amino acid to a substance that does not serve as a substrate of D-amino acid oxidase or D-amino acid acetyltransferase.

More specifically, the method of detecting or measuring homocysteine of the present invention includes the steps of:

(a) reacting a D-amino acid present in a sample with a D-amino acid converting enzyme to convert the D-amino acid to a substance that does not serve as a substrate of D-amino acid oxidase or D-amino acid acetyltransferase;

(b) reducing homocysteine in the sample with a thiol compound;

(c) reacting the reduced homocysteine with a methyltransferase and a methyl donor to newly produce a D-amino acid; and (d) reacting the produced D-amino acid with the D-amino acid oxidase or D-amino acid acetyltransferase in the presence of an SH reagent to produce hydrogen peroxide, and color-developing the produced hydrogen peroxide by using an oxidative color-developing agent.

Any sample can be used as a sample to be subjected to detect or measure homocysteine by the method of the present invention, as long as it is believed to contain homocysteine. The homocysteine can be present in the form of, not only reduced homocysteine, but also oxidized homocysteine that is bound to another molecule by a disulfide bond such as a complex with a protein, a homocysteine dimer and a homocysteine-cysteine dimer. For example, serum, plasma, blood, urine and a dilution thereof can be used.

Step (a):

As the D-amino acid converting enzyme that is used in the method of the present invention, any D-amino acid converting enzyme can be used, as long as it can react with a D-amino acid to convert the D-amino acid into a substance that does not serve as a substrate of D-amino acid oxidase or D-amino-acid acetyltransferase so as to lead it to the outside of the reaction system of the homocysteine measurement. In the present invention, a D-amino acid converting enzyme that can react with D-alanine and/or D-serine is preferable. As an enzyme that reacts with D-alanine, D-alanyl-D-alanine ligase [EC 6.3.2.4], D-alanine hydroxylmethyltransferase [EC 2.1.2.7], D-alanine-y-glutamyl-transferase [EC 2.3.2.14], or the like can be used. As an enzyme that reacts with D-serine, D-serine dehydratase [EC 4.3.1.18], diaminopropionate ammonia-lyase [EC 4.3.1.18], or the like can be used. These enzymes can be used alone or in combination if necessary. As the enzyme that reacts with D-alanine, D-alanyl-D-alanine ligase is preferably used, and as the enzyme that reacts with D-serine, D-serine dehydratase is preferably used.

Any D-alanyl-D-alanine ligase (Ddl) derived from any sources can be used in the method of the present invention, enzymes, as long as it can condense two D-alanine molecules to produce D-alanyl-D-alanine. For example, Ddls derived from almost all bacteria can be utilized. Enzymes derived from *E. coli* are preferable. "*E. coli*" in this specification refers to *Escherichia coli* described in Bergey's Manual of Determinative Bacteriology, the 8th edition (edited by R. E. Buchanan and N. E. Gibbons, The Williams & Wilkins Company, Baltimore, pp. 295–296, 1974) and its variants and modified forms.

As Ddl used in the method of the present invention, enzymes derived from *E. coli* having an amino acid sequence estimated from the base sequence of GenBank Accession No. J05319 described in Biochemistry 30:1673–1682 (1991) or GenBank Accession No. AE000118 REGION: 18688..19608 described in Journal of Bacteriology 167: 809–817 (1986) are preferably used. Furthermore, enzymes derived from microorganisms belonging to the genus of *Bacillus, Enterococcus, Lactobacillus* and the like also can be used. The sequence can be modified in some amino acids (e.g., addition, deletion or substitution of one or more amino acids), as long as the Ddl activity does not disappear. The Ddl can be obtained by any methods well-known to those skilled in the art, for example, by a method of preparing a crude enzyme from the *E. coli* (e.g., an *E. coli* strain that has been transformed by introducing ddl gene obtained from bacteria or the like) and then purifying it by, for example, various chromatography techniques.

The D-serine dehydratase (Dsd) used in the method of the present invention is an enzyme also called D-serine ammonia-lyase, D-serine dehydrase, D-hydroxyamino acid dehydratase, D-serine hydrase, or D-serine deaminase. Dsd derived from any sources can be used, as long as it can deaminate D-serine to produce pyruvic acid. Enzymes derived from *E. coli* having an amino acid sequence estimated from the base sequence of GenBank Accession No. J01603 described in J. Bacteriol. 154(3), 1508–1512 (1983) are preferably used. Furthermore, Dsds derived from microorganisms belonging to the genus of *Pseudomonas, Bacillus, Salmonella, Fusobacterium, Vibrio, Shigella, Ralstonia* and the like can be used. The sequence can be modified in some amino acids (e.g., addition, deletion or substitution of one or more amino acids), as long as the Dsd activity does not disappear. The Dsd can be obtained by any methods well-known to those skilled in the art, for example, by a method of preparing a crude enzyme from *E. coli* (e.g., an *E. coli* strain that has been transformed by introducing dsd gene obtained from bacteria or the like) and then purifying it by, for example, various chromatography techniques.

The ddl gene and the dsd gene can be obtained by a method commonly used by those skilled in the art, based on the estimated amino acid sequences described above. For example, methods performing plaque hybridization, colony hybridization, PCR or the like can be employed, where a part or all of the genes encoding Ddl or Dsd or genes containing these sequences are used as probes. The gene source of Ddl or Dsd is not limited to *E. coli,* but other species of bacteria can be used as well.

In this specification, "ddl gene" refers to a DNA chain or DNA sequence that encodes a polypeptide having the Ddl activity that exhibits the characteristics of Ddl, and "dsd gene" refers to a DNA chain or DNA sequence that encodes a polypeptide having the Dsd activity that exhibits the characteristics of Dsd. In both cases, a polypeptide having a modification (e.g., addition, deletion or substitution) in the amino acid sequence that does not affect the activity of the enzyme as described above may be encoded. Moreover, a plurality of sequences may encode the same polypeptide, for example, due to degeneracy. Furthermore, the ddl gene or the dsd gene may be derived from natural sources or may be totally synthesized or semi-synthesized chemically.

The obtained ddl gene or the dsd gene is, for example, ligated to an expression vector that can multiplicate and is introduced into a host such as *E. coli*. The expression vector used herein may be any expression vector, as long as it can be usually used for *E. coli*, and for example, ColE1, pCR1, pBR322, pMB9 and the like can be preferably used.

In order to express a large amount of DNA encoding Ddl or Dsd in *E. coli*, or to increase the expression amount thereof, a promoter for controlling transcription and translation may be incorporated into a 5' upstream region of the DNA chain of the vector, and/or a terminator may be incorporated into a 3' downstream region thereof. Such a promoter and/or a terminator may be derived from a ddl gene or dsd gene itself, derived from a gene that is well known such as β-galactosidase gene, or obtained by artificially modifying these known genes. Therefore, expression vectors in which such control sequences are incorporated are preferably used as the expression vector, and examples thereof include pTrc99A, pKK223-3 (which are manufactured by Amersham Pharmacia Biotech), and pET3, pET-11 (which are manufactured by Stratagene), although there is no limitation to these vectors.

Any microorganisms can be used as a host for expressing Ddl or Dsd, but bacteria are preferable and *E. coli* is more preferable. A transformant for expressing Ddl or Dsd can be produced by a method known in the field of genetic engineering, for example, by a rubidium chloride method (J. Mol. Biol., 166:557, 1983). The thus obtained transformant of *E. coli* whose ability of expressing Ddl or Dsd is increased is cultured so that Ddl or Dsd can be obtained.

The Ddl or Dsd obtained in the above-described manner may be used alone or in combination.

When Ddl is applied to a reagent for measuring homocysteine, the produced D-alanyl-D-alanine can not be a substrate of D-amino acid oxidase, so that it is possible to eliminate the D-alanine contained in a sample. There is no limitation regarding the amount of enzyme used, as long as it has a concentration that can eliminate the D-alanine in the sample, and for example, the amount can be 0.01 to 100 U/mL, and preferably is 0.1 to 10 U/mL. In the present invention, the amount of Ddl that produces 1 μmol of D-alanyl-D-alanine per minute at 37° C., using D-alanine as the substrate is defined as 1 unit. There is also no limitation regarding the amounts of ATP and Mg ions to be used that is necessary to exhibit the activities, as long as they have a concentration that can eliminate D-alanine, and for example, for ATP, an amount of 0.1 to 10 mM, and for Mg ions, an amount of 0.1 to 20 mM are preferable. This treatment of a sample with enzymes can be performed alone, or can be performed simultaneously with the following steps (b) and (c).

When Dsd is used as a reagent for measuring homocysteine, D-serine can be removed from the reaction system by converting D-serine contained in a sample into pyruvic acid. There is no limitation regarding the amount of enzyme used, as long as it has a concentration that can eliminate D-serine in the sample, and for example, the amount can be 0.001 to 10 U/mL, and preferably is 0.01 to 1 U/mL. In the present invention, the amount of Dsd that degrades 1 μmol of D-serine per minute at 37° C. is defined as 1 unit. This treatment of a sample with enzymes can be performed alone, or can be performed simultaneously with the following steps (b) and (c).

Step (b):

The step (b) in the method of the present invention is a step of reducing homocysteine in various forms in a sample with a thiol compound into a reduced homocysteine.

The thiol compound used in the method of present invention is not particularly limited, and includes, for example, dithiothreitol, mercaptoethanol, N-acetylcysteine, dithioerythritol, and thioglycolic acid. Any concentration of the thiol compound may be employed as the concentration of the thiol compound, as long as it is in a range that allows oxidized homocysteine to reduced homocysteine. Preferably, the concentration is 0.1 mM or more in terms of thiol groups, and more preferably 1 mM or more.

Step (c):

The step (c) in the method of the present invention is a step of reacting the reduced homocysteine made in the step (b) above with a methyltransferase and a methyl donor so as to newly produce D-amino acid. In the present invention, a methyltransferase using homocysteine as a methyl acceptor is preferably used, and D-methionine methylsulfonium is preferably used as a methyl donor. That is, the reduced homocysteine in the sample is reacted with a methyltransferase and D-methionine methylsulfonium to produce D-methionine.

There is no limitation regarding the methyltransferase, as long as it reacts with D-methionine methylsulfonium to catalyze the production of D-methionine. Examples of the methyltransferase include homocysteine methyltransferase [EC 2.1.1.10], 5-methyltetrahydrofolic acid-homocysteine S-methyltransferase [EC 2.1.1.13], and 5-methyl-tetrahydropteroyltriglutamic acid-homocysteine S-methyltransferase [EC 2.1.1.14]. Preferably, homocysteine methyltransferase [EC 2.1.1.10] can be used. This enzyme produces D-methionine, using D-methionine methylsulfonium as a methyl donor, in spite of its low specificity, as reported by G. Grue-Sorensen et al (J. Chem. Soc. Perkin Trans. I 1091-7 (1984)). The homocysteine methyltransferase to be used may be derived from any sources, as long as it uses D-methionine methylsulfonium as a methyl donor. For example, enzymes derived from bacteria, yeasts, rats or the like can be used. In the present invention, the amount of the homocysteine methyltransferase that produces 1 μmol of D-methionine per minute at 37° C., using homocysteine and D-methionine methylsulfonium as the substrates, is defined as 1 unit.

Step (d):

The step (d) in the method of the present invention is a step of reacting the D-amino acid produced in the step (c) with D-amino acid oxidase or D-amino acid acetyltransferase in the presence of an SH reagent to produce hydrogen peroxide, and color-developing the produced hydrogen peroxide by using an oxidative color-developing agent.

When D-amino acid is reacted with D-amino acid oxidase [EC 1.4.3.3], hydrogen peroxide is produced. This is led to an oxidative color-developing agent commonly used in the presence of an SH reagent so as to be determined calorimetrically. The D-amino acid oxidase may be derived from any sources. For example, it may be derived from animal organs, bacteria, or fungi. Preferably, those derived from porcine kidney can be used. In the present invention, the amount of the D-amino acid oxidase that converts 1 μmol of D-alanine into pyruvic acid per minute at 37° C. is defined as 1 unit.

When D-amino acid is reacted with D-amino acid acetyltransferase [EC 2.3.1.36], coenzyme A is produced. Coenzyme A is reacted with acyl-coenzyme A synthetase [EC 6.2.1.3] and acyl-coenzyme A oxidase [EC 1.3.3.6], sequencially, then hydrogen peroxide is produced. The produced hydrogen peroxide can be quantitatively determined in the same manner. The D-amino acid acetyltransferase may be derived from any sources. For example, those derived from yeasts can be used.

Examples of the SH reagent include an oxidizing agent such as Ellman's reagent, a mercaptido forming agent such as p-mercuri benzoic acid, and an alkylating agent such as iodoacetic acid and N-ethylmaleimide, as described in Biochemistry Dictionary (3$^{rd}$ edition, p. 182, Tokyo Kagaku Doujin, 1998). Preferably, an alkylating agent, and more preferably a maleimide compound, and most preferably, N-ethylmaleimide can be used.

The produced hydrogen peroxide can develop the color of an ordinary oxidative color-developing agent with peroxidase. As the oxidative color-developing agent, various Trinder reagents can be used in combination with a coupler reagent. This method is called the Trinder method, and is commonly used in the field of clinical chemical analysis, which is not described herein in detail. It is preferable to use 4-aminoantipyrine as the coupler reagent and to use ADOS [N-ethyl-N-(2-hydroxy-3-sulfopropyl)-3-methoxyaniline], DAOS [N-ethyl-N-(2-hydroxy-3-sulfopropyl)-3,5-dimethoxyaniline], HDAOS [N-(2-hydroxy-3-sulfopropyl)-3,5-dimethoxyaniline], MAOS [N-ethyl-N-(2-hydroxy-3-sulfopropyl)-3,5-dimethylaniline], TOOS [N-ethyl-N-(2-hydroxy-3-sulfopropyl)-3-methylaniline] or the like as the Trinder reagent. Furthermore, a leuco-type color-developing agent such as o-tolidine, o-dianisidine, DA-67 [10-(carboxymethylaminocarbonyl)-3,7-bis(dimethylamino)phenothiazine sodium, manufactured by Wako Pure Chemical Industries Ltd.], and TPM-PS [N,N,N',N',N'',N''-hexa(3-sulfopropyl)-4,4',4''-triaminotriphenylmethane hexasodium salt, Dojindo Laboratories], which do not require the coupler reagent, can be used as well. In particular, DA-67 and TPM-PS have a mole absorption coefficient larger than that of the Trinder reagent, so that the determination can be performed with higher sensitivity.

Reagent kit for homocysteine measurement:

The present invention provides a reagent kit for homocysteine measurement including (a) D-alanyl-D-alanine ligase and/or D-serine hydratase, (b) a thiol compound, (c) a methyltransferase and a methyl donor, and (d) D-amino acid oxidase or D-amino acid acetyltransferase+acyl-coenzyme A synthetase+acyl-coenzyme A oxidase, an SH reagent, and an oxidative color-developing agent. In general, these (a) to (d) are provided separately, but (a) to (c) may be provided as a reagent for measurement that is previously prepared by mixing in a buffer solution.

Hereinafter, the present invention will be described more specifically by way of examples, but the present invention is not limited by the following examples.

EXAMPLE 1

Preparation of Recombinant D-alanyl-D-alanine Ligase (A) (DdlA) Derived from *E. coli*

(1-1) Synthesis of Probes and Obtainment of ddlA Gene

Synthetic primers shown in SEQ ID NOS: 1 and 2, which include EcoRI and PstI recognition sites, respectively, were synthesized based on the base sequence information of the ddlA gene from *E. coli* encoding an enzyme having DdlA activity (Biochemistry 30:1673–1682 (1991), GenBank Accession No. J05319). PCR was performed in a buffer solution (2 μl of KOD DNA polymerase (manufactured by TOYOBO Co., Ltd.; hereinafter, referred to as "KOD"), 10 μl of 10×KOD buffer solution, 10 μl of dNTP mixture, 5 μl of DMSO and 5 μl of distilled water), using these primers in an amount of 3 nmol (100 pmol/μl, 30 μl) each, and using 2 μl of chromosomal DNA of *E. coli* JM109 as a template to give 1.09 kb DNA containing the DdlA structural gene.

(1-2) Preparation of Plasmid Including ddlA Gene

The thus obtained ddlA gene was ligated to a SmaI fragment of *E. coli* vector pUC19 having DNA replication origin of *E. coli* ColE1 and ampicillin resistance gene, and introduced in *E. coli* JM109 by the rubidium chloride method (J. Mol. Biol., 166:557, 1983) to give a transformant having a recombinant plasmid containing the ddlA gene. All the restriction enzymes used in the Examples were obtained from TAKARA BIO INC.

Using the recombinant plasmid in the transformant, the base sequence was determined by using 377 Automate Sequencing System (manufactured by PerkinElmer Co., Ltd.) based on the dideoxy terminator method using fluorescent-labeled primers. The ddlA has a structural gene region with 1095 bases, and encodes 364 amino acids, which was completely consistent with the above-described base sequence information on the ddlA gene.

(1-3) Preparation of Expression Vector and Transformant Including ddlA Gene

Figure 2:
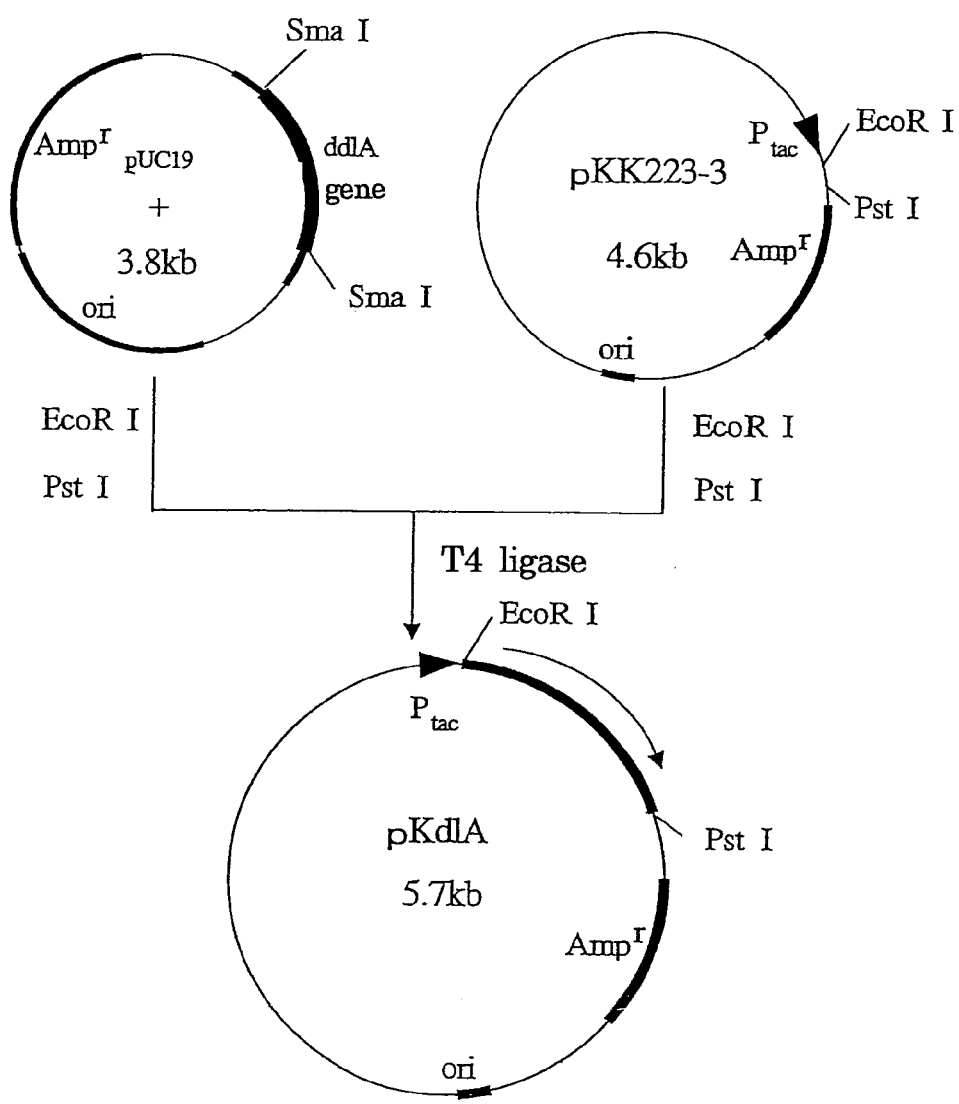
FIG. 2 is a schematic diagram showing construction of expression vector pKdlA.

The above-described recombinant plasmid was digested with restriction enzymes EcoRI and PstI to give a DNA fragment, and then the 1.09 kb DNA fragment containing the ddlA DNA was purified by agarose gel electrophoresis. *E. coli* vector pKK233-3 (manufactured by Amersham Pharmacia Biotech) having ampicillin resistance gene was digested with restriction enzymes EcoRI and PstI, and ligated to the obtained 1.09 kb DNA fragment to give an expression vector pKdlA (see FIG. 2). This expression vector pKdlA is induced to express DdlA by isopropyl-β-D-thiogalactopyranoside (hereinafter, referred to as "IPTG").

The obtained expression vector pKdlA was introduced into *E. coli* JM109 by the rubidium chloride method, and one in which DdlA is expressed was selected to give a transformant JM109-ddlA-3.

(1-4) Confirmation of Activity of Expressed DdlA

The obtained transformant JM109-ddlA-3 was cultured in 3 ml of LB liquid medium (1% yeast extract, 2% bactopeptone, and 2% glucose) containing ampicillin at 37° C. for about four hours with shaking. A 0.3 ml aliquot was added to 10 ml of LB liquid medium and cultured at 37° C. for three hours with shaking, and IPTG (TAKARA BIO INC.) was added thereto such that the final concentration became 1 mM, and was cultured further for four hours. The culture was centrifuged at 8000 rpm for 15 minutes to collect cells. Then, after the cells were washed with 1 ml of 100 mM Bis-tris-HCl buffer solution (pH 7.4) once, they were suspended in a solubilzation solution (100 mM Bis-tris-HCl buffer solution (pH 7.4), 1 mM EDTA, 5 mM MgCl$_2$, and 100 μg/ml lysozyme) in a volume ten times that of the cells. The suspension was treated twice with an ultrasonic generator (UD-200 manufactured by TOMY SEIKO Co., Ltd.) at scale 1 for 10 seconds to disrupt the cells. A supernatant was obtained by centrifugation at 15000 rpm for 10 minutes, and this was used as a sample for measuring the Ddl activity. As a control, a transformant of *E. coli* JM109 strain with non-recombinant pKK223-3 that had been treated in the same manner was used.

The enzyme activity was measured in the following manner. First, a reagent for measuring the activity (100 μl of 20 mM D-alanine, 20 mM ATP, 100 mM HEPES, 40 mM MgCl$_2$, and 50 μl of 40 mM KCl) was added to the disrupted cell solution (50 μl), and allowed to react at 37° C. for one hour. Then, 2 μl of the reaction mixture was spotted onto a silica gel thin layer, and then developed using ethanol:25% aqueous ammonia=74:26 (w/w) as an eluent in a closed vessel. After development, a ninhydrin solution (0.1 M citric acid buffer solution saturated with n-butanol, which contains 0.2% of ninhydrin) was sprayed to detect the produced D-alanyl-D-alanine. The D-alanyl-D-alanine was produced in the disrupted recombinant cell solution in a significantly larger amount compared to the disrupted control cell solution.

(1-5) Preparation of DdlA

The recombinant *E. coli* obtained in the above steps (1–3), which has high production ability of DdlA, was inoculated in 200 ml of LB medium (1% yeast extract, 2% bactopeptone, and 2% glucose) containing ampicillin and was cultured at 37° C. for 15 hours. Then, the culture was inoculated to 1.8 L of LB medium containing ampicillin in a jar fermenter with a volume of 5 L, and cultured at 37° C. for 100 minutes with aeration and stirring. To the culture, IPTG was added such that the final concentration became 1 mM, and cultured further for 4 hours. The culture was centrifuged at 8000 rpm for 10 minutes to collect cells. The cells were suspended in a buffer solution (20 mM Bis-tris-HCl buffer solution (pH 7.4), 1 mM EDTA, and 5 mM $MgCl_2$) in a volume nine times that of the cells. The suspension was treated with an ultrasonic generator (UD-200 manufactured by TOMY SEIKO CO., Ltd.) to disrupt the cells. Then, the suspension was centrifuged at 15000 rpm for 10 minutes to remove the debris and thus a crude enzyme solution was obtained.

Ammonium sulfate was added to the obtained crude enzyme solution so as to be 5% saturation under ice cooling with stirring, and thereafter was allowed to stand for 30 minutes, and then was centrifuged at 14000 rpm. Ammonium sulfate was added to the obtained supernatant so as to be 45% saturation under ice cooling with stirring, and thereafter allowed to stand for 30 minutes, and then centrifuged at 14000 rpm. The obtained precipitate was dialyzed overnight against a buffer solution (20 mM Bis-tris-HCl buffer solution (pH 7.4), 1 mM EDTA, and 5 mM $MgCl_2$).

Then, the dialyzed crude enzyme solution was purified by column chromatography (adsorption: a buffer solution A (20 mM Bis-tris-HCl buffer solution (pH 7.4), 1 mM EDTA, and 5 mM $MgCl_2$), elution: a buffer solution A—0.0 to 0.6 M sodium chloride gradient) using Q-SEPHAROSE FF (manufactured by Amersham Pharmacia Biotech). The Ddl active fractions were collected and further purified by gel filtration column chromatography with SEPHACRYL S-100 (manufactured by Amersham Pharmacia Biotech). The obtained active fractions were subjected to SDS-polyacryl amide gel electrophoresis and stained by Coomassie brilliant blue, which confirmed that the DdlA was purified to substantially a single band.

EXAMPLE 2

Preparation of Recombinant D-alanyl-D-alanine Ligase (B) (DdlB) Derived from *E. coli*

(2-1) Synthesis of Probe and Acquisition of ddlB Gene

Synthetic primers shown in SEQ ID NOS: 3 and 4 were synthesized, based on the base sequence information of the ddlB gene of *E. coli* encoding an enzyme having the DdlB activity (Journal of Biochemistry 167:809–817 (1986), GenBank Accession No. AE000118 REGION: 18688..19608). PCR was performed in a buffer solution (2 μl of KOD, 10 μl of 10×KOD buffer solution, 10 μl of dNTP mixture, 5 μl of DMSO and 5 μl of distilled water), using these primers in an amount of 3 nmol (100 pmol/μl, 30 μl) each, and using 2 μl of chromosome DNA of *E. coli* JM109 as a template to give 0.92 kb DNA containing the DdlB structural gene.

(2-2) Preparation of Plasmid Including ddlB Gene

The thus obtained ddlB gene was ligated to a SmaI fragment of an *E. coli* vector pUC19 having DNA replication origin of *E. coli* ColE1 and an ampicillin resistance gene, and introduced into *E. coli* JM109 by the rubidium chloride method (J. Mol. Biol., 166:557, 1983) to give a transformant having a recombinant plasmid containing the ddlB gene.

Using the recombinant plasmid in the transformant, the base sequence was determined by using 377 Automate Sequencing System (manufactured by PerkinElmer Co., Ltd.) based on the dideoxy terminator method using fluorescent-labeled primers. The ddlB has a structural gene region with 921 bases, and encodes 306 amino acids, which was completely consistent with the base sequence information on the ddlB gene.

(2-3) Preparation of Expression Vector and Transformant Including ddlB Gene

Figure 3:
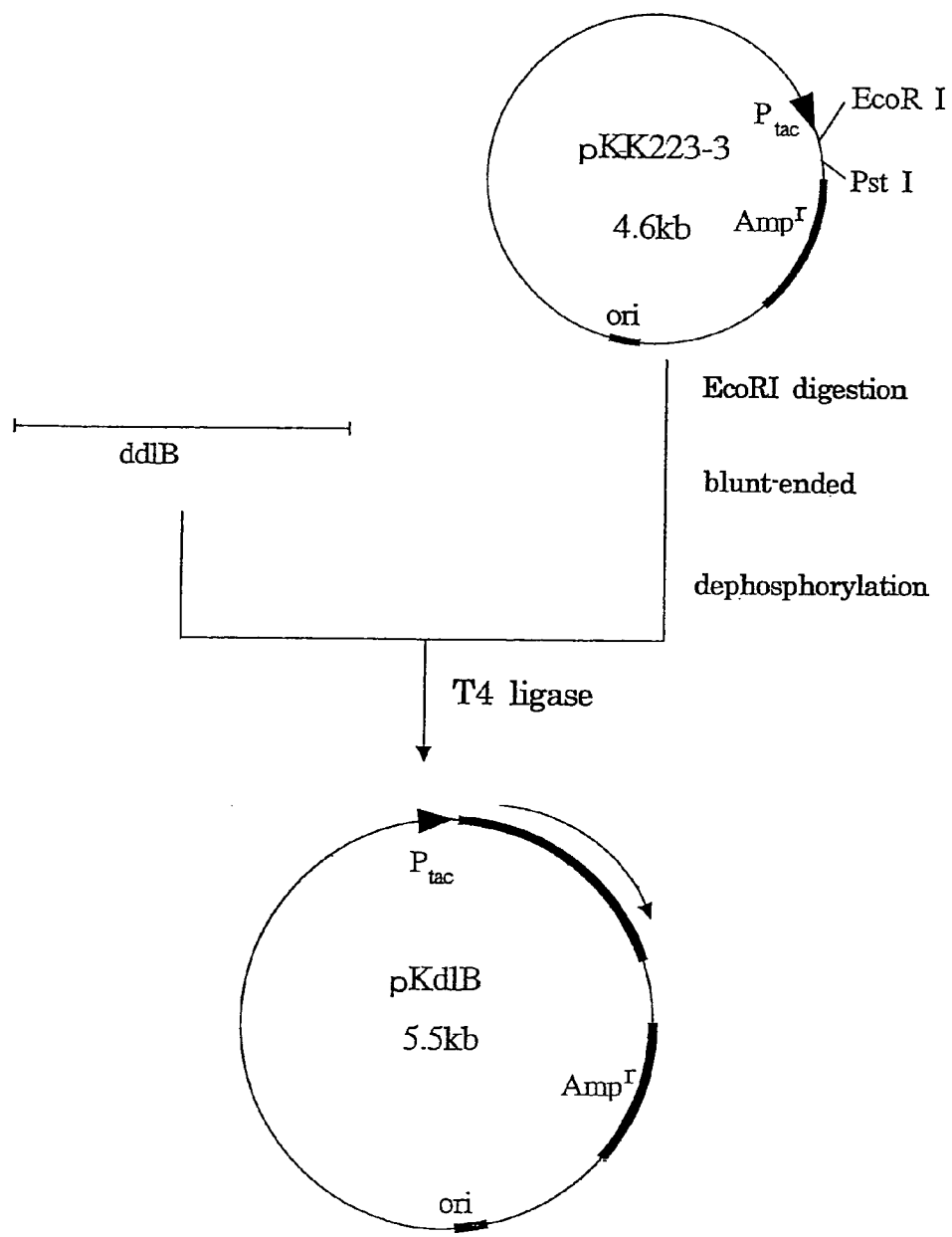
FIG. 3 is a schematic diagram showing construction of expression vector pKdlB.

An *E. coli* vector pKK233-3 (manufactured by Amersham Pharmacia Biotech) was digested with restriction enzymes EcoRI, and blunt-ended using DNA Blunting Kit (manufactured by TAKARA BIO INC.), then dephosphorylated using alkaline phosphatase (manufactured by TAKARA BIO INC.), and a fragment of the DdlB structural gene obtained in (2-1) was ligated thereto to give an expression vector pKdlB (see FIG. 3). This expression vector pKdlB is induced to express DdlB by IPTG.

The obtained expression vector pKdlB was introduced into *E. coli* JM109 by the rubidium chloride method, and one in which DdlB is expressed was selected to give a transformant JM109-ddlB-1.

(2-4) Preparation of DdlB

The recombinant *E. coli* obtained in the above steps (2-3), which has high production capacity of DdlB, was inoculated in 200 ml of LB medium (1% yeast extract, 2% bactopeptone, and 2% glucose) containing ampicillin and was preliminarily cultured at 37° C. for 15 hours. The culture was inoculated to 1.8 L of LB medium containing ampicillin in a jar fermenter with a volume of 5 L, and cultured at 37° C. for 100 minutes with aeration and stirring. To the culture, IPTG was added such that the final concentration became 1 mM and the culture was cultured further for 4 hours. The culture was centrifuged at 8000 rpm for 10 minutes to collect the cells. The cells were suspended in a buffer solution (20 mM Bis-tris-HCl buffer solution (pH 7.2), 1 mM EDTA, and 5 mM $MgCl_2$) in a volume nine times that of the cells. The suspension was treated with an ultrasonic generator (UD-200 manufactured by TOMY SEIKO CO., Ltd.) to disrupt the cells. Then, the suspension was centrifuged at 15000 rpm for 10 minutes to remove the debris and thus a crude enzyme solution was obtained.

Ammonium sulfate was added to the obtained crude enzyme solution so as to be 25% saturation under ice cooling with stirring, and thereafter was allowed to stand for 30 minutes, and then centrifuged at 14000 rpm. Ammonium sulfate was added to the obtained supernatant so as to be 50% saturation under ice cooling with stirring, and thereafter allowed to stand for 30 minutes, and then centrifuged at 14000 rpm. The obtained precipitate was dialyzed overnight against a buffer solution (20 mM Bis-tris-HCl buffer solution (pH 7.2), 1 mM EDTA, and 5 mM $MgCl_2$).

Then, the dialyzed crude enzyme solution was purified by column chromatography (adsorption: a buffer solution A (20 mM Bis-tris-HCl buffer solution (pH 7.2), 1 mM EDTA, and 5 mM MgCl2), elution: a buffer solution A—0.0 to 0.6 M sodium chloride gradient) using Q-SEPHAROSE FF (manufactured by Amersham Pharmacia Biotech). The Ddl active fractions were collected and further purified by gel filtration column chromatography with SEPHACRYL S-100 (manufactured by Amersham Pharmacia Biotech). The obtained active fractions were subjected to SDS-polyacryl amide gel electrophoresis and stained by Coomassie brilliant blue, which confirmed that the DdlB was purified to substantially a single band.

EXAMPLE 3

Preparation of Recombinant D-serine Dehydratase (Dsd) Derived from *E. coli*

(3-1) Preparation of expression vector and transformant including dsd gene

The following two synthetic primers (SEQ ID NOS: 5 and 6) were synthesized, based on the base sequence information of the dsd gene of *E. coli* encoding an enzyme having the Dsd activity.

PCR was performed, using these primers and using genome DNA of *E. coli* as a template. The obtained DNA fragment was digested with EcoRI and HindIII, and ligated to a vector PUC118 that had been digested with the same restriction enzymes. This was introduced into *E. coli* JM109 by the rubidium chloride method to give a transformant having a recombinant plasmid containing the dsd gene.

(3-2) Preparation of Dsd

The Dsd expressing cell strain obtained in the above-described manner was cultured in about 10 L of LB medium containing 100 μg/ml of ampicillin. Enzyme purification was performed according to the method described in J. Biol. Chem., 263, 16926–16933, 1988. The cell paste was suspended in SPE lysis buffer (20% sucrose, 20 mM EDTA, 30 mM potassium phosphate, 0.5 mg/mL lysozyme, pH7.8) in almost the same volume. After incubation, water containing a protease inhibitor and pyridoxal 5'-phosphorate (PLP) was added thereto for lysis. The lysate was cooled with ice and a buffer solution B (1M potassium phosphate, 800 μM PLP, 50 mM EDTA, 10 mM DTT, pH7.5) was added thereto in almost the same volume, and the cell debris was removed by centrifugation at 18000 rpm for 30 minutes. The obtained supernatant was adjusted to pH 7.3, and nucleic acid was precipitated by 1% Polymin P and then centrifuged to give supernatant. Ammonium sulfate was added thereto and dissolved therein so as to be 70% saturation. Then, the solution was stirred for 40 minutes and then centrifuged at 18000 rpm for two hours. The obtained precipitate was suspended in a small amount of buffer solution C (10 mM potassium phosphate, 80 μM PLP, 1 mM EDTA, 1 mM DTT, pH 7.2) and dialyzed overnight against the same buffer solution.

Then, the dialyzed crude enzyme solution was purified by column chromatography using DEAE-TOYOPEARL (manufactured by Tosoh Corporation). For adsorption, the buffer solution C was used, and elution was performed using 0 to 200 mM KCl gradient in this buffer solution. The Dsd active fractions were collected and precipitated with 70% saturated ammonium sulfate and recovered. The recovered fractions were dissolved in a small amount of the buffer solution C, and dialyzed overnight against the same buffer solution to remove ammonium sulfate. Furthermore, they were dialyzed against a buffer solution D (1 mM potassium phosphate, 1 mM DTT, pH7.0) for 3 to 4 hours.

The dialyzed partially purified enzyme solution was further purified by hydroxyapatite column chromatography (Gigapite, manufactured by TOAGOSEI CO., LTD., available from SEIKAGAKU CORPORATION). This enzyme solution was applied to a column previously equilibrated with the buffer solution D, washed with the same buffer solution in a volume three times the column, and eluted with a buffer solution E (10 mM potassium phosphate, 80 μm PLP, 1 mM EDTA, pH7.8). A buffer solution in a volume of 1/10 was added to each eluted fraction, and Dsd active fractions were collected, precipitated with 70% saturated ammonium sulfate and recovered. The obtained precipitate was suspended in a small amount of buffer solution F (100 mM potassium phosphate, 80 μm PLP, 1 mM EDTA, 1 mM DTT, pH7.8), and dialyzed against this buffer solution to give a purified enzyme.

(3-3) Measurement of Dsd Activity

The Dsd activity was determined by measuring coupling of the pyruvic acid produced from D-serine with lactate dehydrogenase in the presence of NADH. More specifically, 0.01 to 0.1 U Dsd was added to 100 mM D-serine, 0.5 mM NADH and 5 U lactate dehydrogenase at 37° C. to initiate a reaction, and a decrease of the absorbance at 340 nm was traced.

EXAMPLE 4

Prevention of Influence of D-alanine by DdlA, DdlB and Dsd

Samples (1 to 5) were prepared in the following manner:
Sample 1: Normal control blood serum SERACLEAR HE (manufactured by Azwell Co. Ltd.)
Sample 2: Addition of 25 μM of homocystine (corresponding to 50 μM of homocysteine) to the sample 1
Sample 3: Addition of 100 μM of D-alanine to the sample 2
Sample 4: Addition of 500 μM of D-serine to the sample 2
Sample 5: Addition of 100 μM of D-alanine and 500 μM of D-serine to the sample 2

First reagents (I to V) and a second reagent were prepared in the following manner:

First Reagent:
Reagent I: 50 mM Bicine (pH 8.0), 123 U/L homocysteine methyltransferase (derived from bacteria), 5.6 mM dithiothreitol, 0.06 mM D-methionine methylsulfonium, 1 mM zinc bromide, 0.3 mM DA-67, 1 mM ATP, 1 mM magnesium chloride
Reagent II: Addition of 0.2285 mg protein/mL of DdlB to the reagent I
Reagent III: Addition of 2.0875mg protein/mL of DdlA to the reagent I
Reagent IV: Addition of 1 U/mL of Dsd to the reagent I
Reagent V: Addition of 0.2285 mg protein/mL of DdlB and 1U/mL of Dsd to the reagent I at the same time Second Reagent:
A reagent containing 50 mM citric acid (pH 5.6), 23 mM NEM, 6.4 U/mL D-amino acid oxidase derived from porcine kidney, and 5.5 U/mL peroxidase Measurement was performed using Hitachi 7170 in the following manner. Any one of the first reagents in an amount of 180 μL was added to each of the samples 1 to 5 in an amount of 15 μL, and allowed to react at 37° C. for 5 minutes. Then, 120 μL of the second reagent was added thereto, and further allowed to react at 37° C. for 5 minutes. The absorbance change (dominant wavelength 660 nm, secondary wavelength 750 nm) from the detection point 16th to 34th was measured.

First, the absorbance change for the samples 1 and 2 were measured with the reagents I to V, respectively, and the measurement sensitivity with respect to the homocysteine added to the samples in each case was taken as 100%. Then, the absorbance change for the samples 3 to 5 were measured with the reagents I to V. The measurement sensitivities of the samples 3 to 5 were shown in Table 1.

TABLE 1

| | | Sample 3 D-Ala | Sample 4 D-Ser | Sample 5 D-Ala + D-Ser |
|---|---|---|---|---|
| Reagent I | Control | 148% | 123% | 169% |
| Reagent II | D-alanyl-D-alanine ligase (B) (DdlB) | 112% | 119% | 128% |
| Reagent III | D-alanyl-D-alanine ligase (A) (DdlA) | 103% | 117% | 117% |
| Reagent IV | D-serine dehydratase (Dsd) | 148% | 100% | 147% |
| Reagent V | DdlB + Dsd | 112% | 101% | 112% |

As seen from these results, in the control, because of the influence of D-alanine and D-serine, the measurement value was high, whereas when DdlB or DdlA was contained in the measurement reagent, the influence of D-alanine in the sample was reduced, and when Dsd was contained, the influence of D-serine in the sample was reduced. Furthermore, it is evident that when both are used simultaneously, the influence of D-alanine and D-serine can be reduced at the same time.

EXAMPLE 5

Elimination of D-alanine and D-serine by Ddl and Dsd

Samples (four types) were prepared in the following manner:
Sample 1: Normal control serum SERACLEAR HE (manufactured by Azwell Co. Ltd.)
Sample 2: Addition of 25 µM of homocystine (corresponding to 50 µM of homocysteine) to the sample 1.
Sample 6: Addition of 200 µM of D-alanine to the sample 2
Sample 7: Addition of 1000 µM of D-serine to the sample 2

First reagents and a second reagent were prepared in the following manner:
First Reagents:
A reagent in which 0, 0.073, 0.145, 0.29 or 0.58 U/mL of DdlB or 0, 0.125, 0.25 or 0.5 U/ml of Dsd was added to a reagent containing 50 mM Bicine (pH 8.0), 123 U/L homocysteine methyltransferase (derived from bacteria), 5.6 mM dithiothreitol, 0.06 mM D-methionine methylsulfonium, 1 mM zinc bromide, 0.3 mM DA-67, 5 mM ATP, and 10 mM magnesium chloride
Second Reagent:
A reagent containing 50 mM citric acid (pH 5.6), 23 mM NEM, 6.4 U/mL D-amino acid oxidase derived from porcine kidney, and 5.5 U/mL peroxidase Measurement was performed using Hitachi 7170 in the following manner. First, 180 µL of first reagent was added to 15 µL of the sample, and allowed to react at 37° C. for 5 minutes. Then, 120 µL of the second reagent was added thereto, and further allowed to react at 37° C. for 5 minutes. The absorbance change (dominant wavelength 660 nm, secondary wavelength 750 nm) from the detection point 16th to 34th was measured.

Figure 4:
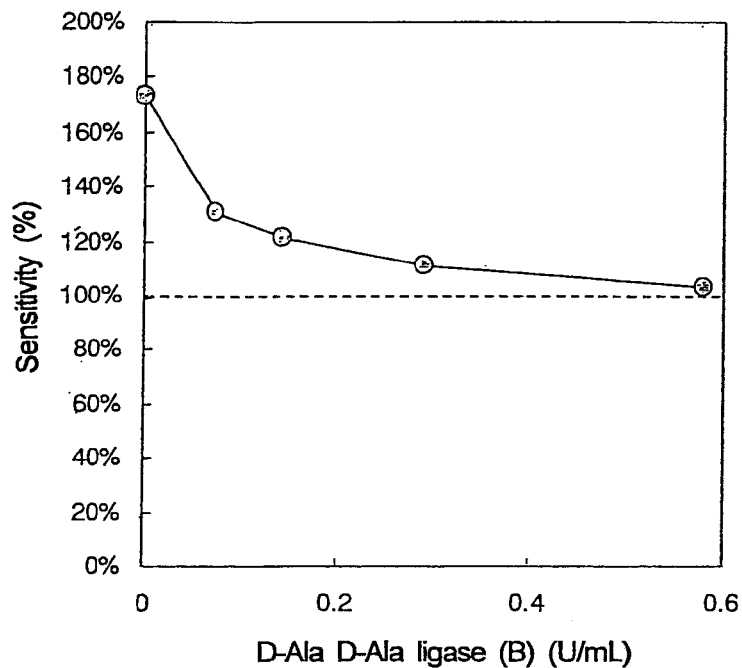
FIG. 4 is a graph showing a relationship between the concentration of D-alanyl-D-alanine ligase and the sensitivity of the homocysteine measurement.
Figure 5:
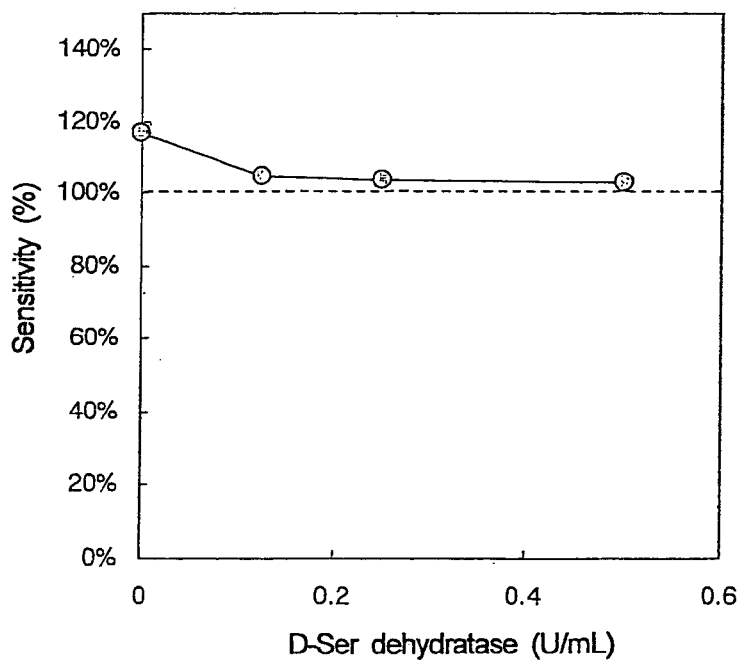
FIG. 5 is a graph showing a relationship between the concentration of D-serine dehydratase and the sensitivity of the homocysteine measurement.

The results are shown in FIGS. 4 and 5.

FIG. 4 shows the concentration of DdlB on the horizontal axis, and the relative sensitivity at the time of homocysteine measurement on the vertical axis. It was confirmed that, by using about 0.5 U/mL of DdlB, the influence of 200 mM D-alanine was substantially prevented.

FIG. 5 shows the concentration of Dsd on the horizontal axis, and the relative sensitivity at the time of homocysteine measurement on the vertical axis. By using about 0.2 U/mL of Dsd, the influence of 1000 mM D-serine was substantially prevented.

EXAMPLE 6

Prevention of Influence of D-amino Acid in a Sample by Ddl and Dsd

Twelve samples of EDTA plasma were used as samples. As the standard, a sample in which 50 µM D-methionine was added to a control blood serum was used.

Three first reagents (i to iii) and a second reagent (used in common) were prepared in the following manner:
First Reagents:
Reagent i: 50 mM Bicine (pH 8.0), 126 U/L homocysteine methyltransferase (derived from bacteria), 5.6 mM dithiothreitol, 0.06 mM D-methionine methylsulfonium, 1 mM zinc bromide, 0.3 mM DA-67
Reagent ii: excluding the homocysteine methyltransferase from the reagent i
Reagent iii: Addition of 5 mM ATP, 10 mM magnesium chloride, 0.58 U/mL DdlB, and 1 U/mL Dsd to the reagent i
Second Reagent:
A reagent containing 50 mM citric acid (pH 5.6), 23 mM NEM, 6.4 U/mL D-amino acid oxidase derived from porcine kidney, and 5.5 U/mL peroxidase Measurement was performed using Hitachi 7170 in the following manner. Any one of the first reagents in an amount of 180 µL was added to 15 µL of the sample, and allowed to react at 37° C. for 5 minutes. Then, 120 µL of the second reagent was added thereto, and further allowed to react at 37° C. for 5 minutes. The absorbance change (dominant wavelength 660 nm, secondary wavelength 750 nm) from the detection point 16th to 34th was measured. The homocysteine concentration in the sample was obtained based on the absorbance change of the standard. The value obtained as a result of measurement with only the reagent A was taken as the value according to the conventional single channel method, the value obtained as a result of taking a difference between measurements with the reagent i and the reagent ii was taken as the value according to the conventional double channel method, and the value obtained as a result of measurement with the reagent iii was taken as the value according to the method of the present invention. Each of these values was compared with the value measured according to the HPLC method.

As seen from FIG. 6, compared with the conventional single channel method, the method of the present invention has an improved correlation with the HPLC method, and exhibits a comparable correlation to the conventional double channel method.

The invention claimed is:

1. A method for detecting or measuring homocysteine in a sample, comprising:
   a) reacting a D-amino acid present in a sample with a D-amino acid converting enzyme to convert the D-amino acid into a substance that does not serve as a substrate of D-amino acid oxidase or D-amino acid acetyltransferase;
   b) reducing homocysteine in the sample with a thiol compound;
   c) reacting the reduced homocysteine with a methyltransferase and a methyl donor to newly produce a D-amino acid; and
   d) reacting the produced D-amino acid with the D-amino acid oxidase or the D-amino acid acetyltransferase in the presence of an SH reagent to produce hydrogen peroxide, and color-developing the produced hydrogen peroxide by using an oxidative color-developing agent.

2. The method of claim 1, wherein the step (a) is a step of reacting D-alanine present in a sample with D-alanyl-D-alanine ligase in the presence of adenosine triphosphate to convert the D-alanine into D-alanyl-D-alanine and/or a step of reacting D-serine present in a sample with D-serine dehydratase to convert the D-serine into pyruvic acid.

3. The method of claim 2, wherein the methyltransferase is homocysteine methyltransferase, and the methyl donor is D-methionine methylsulfonium.

4. The method of claim 3, wherein in the step (d), the produced hydrogen peroxide is detected or measured by color-development using peroxidase and an oxidative color-developing agent.

5. The method of claim 2, wherein in the step (d), the produced hydrogen peroxide is detected or measured by color-development using peroxidase and an oxidative color-developing agent.

6. A reagent kit for measuring homocysteine comprising D-alanyl-D-alanine ligase and/or D-serine dehydratase; a thiol compound; a methyltransferase; a methyl donor; D-amino acid oxidase or D-amino acid acetyltransferase; an SH reagent; and an oxidative color-developing agent.

* * * * *

UNITED STATES PATENT AND TRADEMARK OFFICE
CERTIFICATE OF CORRECTION

| | | |
|---|---|---|
| PATENT NO. | : 7,135,306 B2 | Page 1 of 1 |
| APPLICATION NO. | : 10/546089 | |
| DATED | : November 14, 2006 | |
| INVENTOR(S) | : Esaki et al. | |

It is certified that error appears in the above-identified patent and that said Letters Patent is hereby corrected as shown below:

<u>Face of the Patent:</u>  See Item (73) Assignee: "Alfresa Pharma Corproation" should read -- Alfresa Pharma Corporation --

<u>Column 7</u>, Line 39, "acetyltransterase" should read -- acetyltransferase --

<u>Column 8</u>, Line 48, "solubilzation" should read -- solubilization --

Signed and Sealed this

Seventeenth Day of April, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,135,306 B2 |
| APPLICATION NO. | : 10/546089 |
| DATED | : November 14, 2006 |
| INVENTOR(S) | : Esaki et al. |

It is certified that error appears in the above-identified patent and that said Letters Patent is hereby corrected as shown below:

<u>Column 14</u>, After Line 67, insert the following paragraph:

-- According to the present invention, homocysteine can be measured without being affected by endogenous D-amino acid and without taking a sample blank. That is to say, homocysteine can be measured accurately by simple operations. --

Signed and Sealed this

Twenty-ninth Day of May, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,135,306 B2 | Page 1 of 1 |
| APPLICATION NO. | : 10/546089 | |
| DATED | : November 14, 2006 | |
| INVENTOR(S) | : Esaki et al. | |

It is certified that error appears in the above-identified patent and that said Letters Patent is hereby corrected as shown below:

<u>Column 14</u>, After Line 67, insert the following paragraph:

-- According to the present invention, homocysteine can be measured without being affected by endogenous D-amino acid and without taking a sample blank. That is to say, homocysteine can be measured accurately by simple operations. --

Signed and Sealed this

Twelfth Day of June, 2007

JON W. DUDAS
*Director of the United States Patent and Trademark Office*